Figure 1:
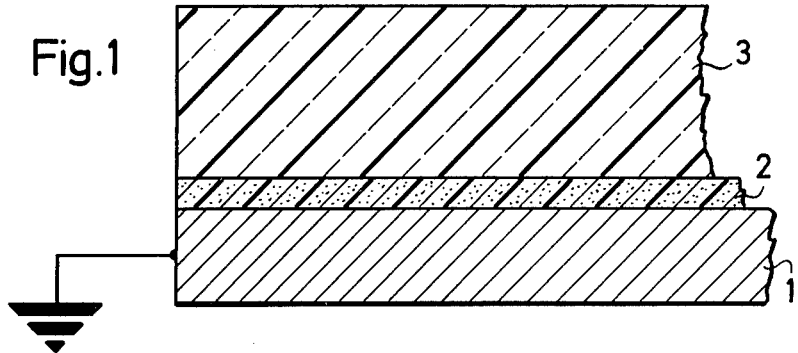

United States Patent

Rochlitz et al.

[11] 4,028,102
[45] June 7, 1977

[54] DIAMINE CONDENSATION PRODUCTS IN DOUBLE LAYER PHOTOCONDUCTIVE RECORDING ELEMENTS

[75] Inventors: Jürgen Rochlitz, Wiesbaden; Reinhard Zunker, Kelkheim, both of Germany

[73] Assignee: Hoechst Aktiengesellschaft, Germany

[22] Filed: Dec. 5, 1975

[21] Appl. No.: 637,929

Related U.S. Application Data

[62] Division of Ser. No. 519,650, Oct. 31, 1974, abandoned.

[30] Foreign Application Priority Data

Nov. 3, 1973 Germany .................. 2355075

[52] U.S. Cl. .................. 96/1.5; 96/1.6; 252/501
[51] Int. Cl.² .................. G03G 5/06
[58] Field of Search .................. 96/1.5–1.7; 252/501; 260/294.8 A, 251 A

[56] References Cited

UNITED STATES PATENTS 3,299,065   1/1967   Dien .................. 260/251 A
3,538,095   11/1970  Christmann et al. .......... 260/251 A

OTHER PUBLICATIONS

Farbwerke Hoechst, Chem. Abstr., vol. 67, No. 109635v, (1967).

Primary Examiner—Edward C. Kimlin
Assistant Examiner—Judson R. Hightower
Attorney, Agent, or Firm—James E. Bryan

[57] ABSTRACT

This invention relates to a compound of the formula

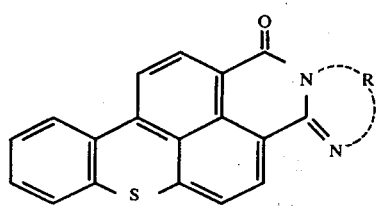

or

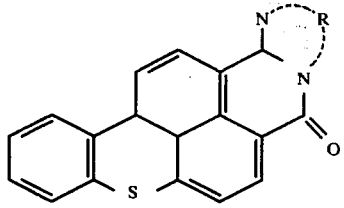

wherein R is a phenylene or naphthylene group. The invention also relates to a process for making the novel compounds of the invention and also to an electrophotographic recording material employing the novel compounds of the invention.

9 Claims, 3 Drawing Figures

Formulae
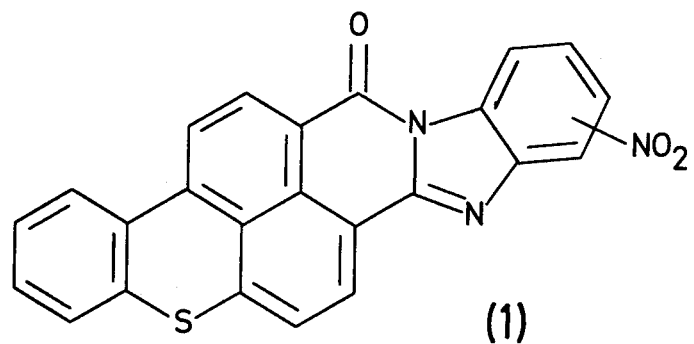
(1)
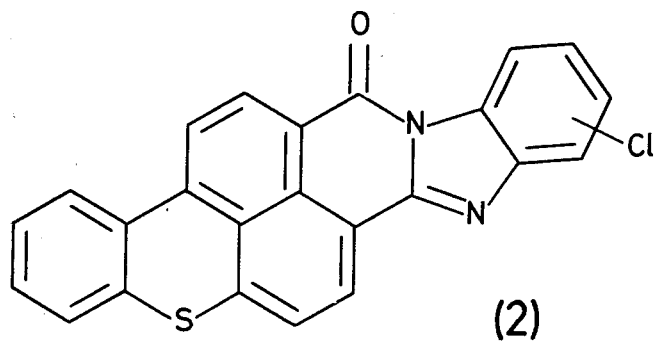
(2)

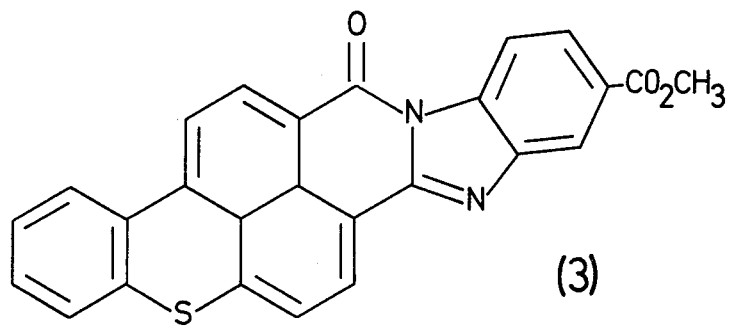
(3)
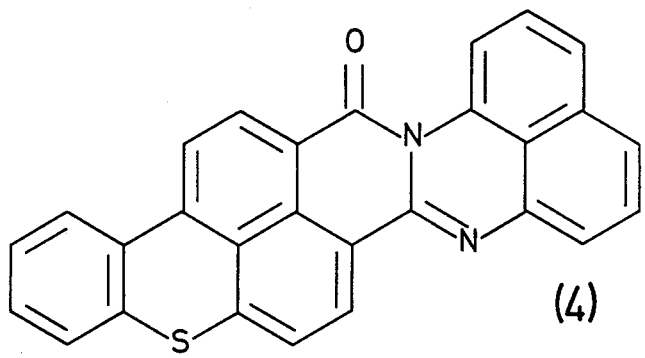
(4)
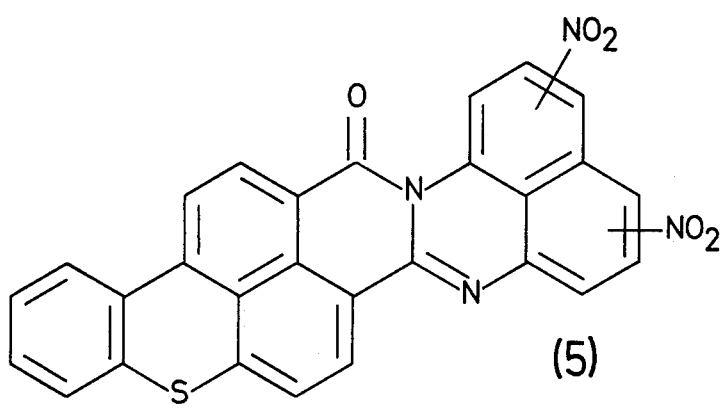
(5)

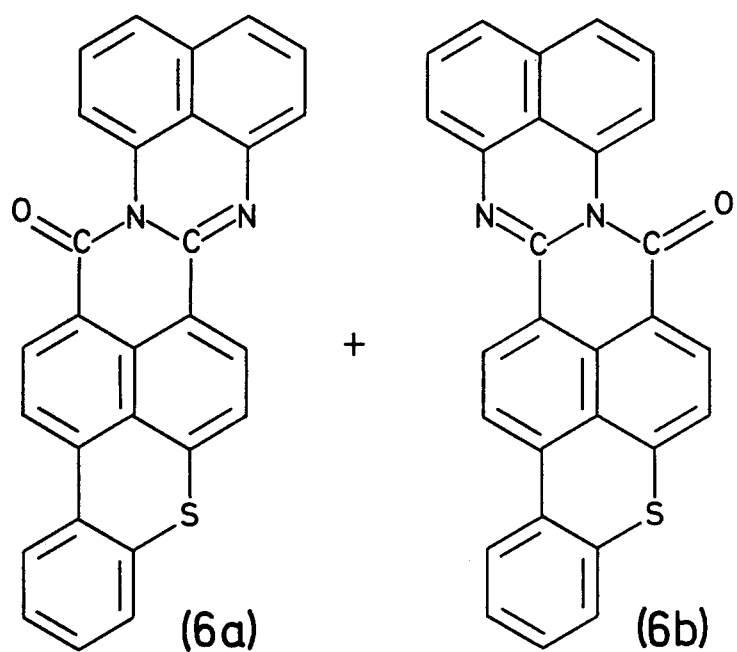

DIAMINE CONDENSATION PRODUCTS IN DOUBLE LAYER PHOTOCONDUCTIVE RECORDING ELEMENTS

This is a division of application Ser. No. 519,650, filed Oct. 31, 1974, now abandoned.

The invention concerns condensation products of diamines and dianhydrides and a method of producing them. The condensation products are useful as homogeneous pigment layers, having high covering capacity, in electrophotographic recording materials with photoconductive double layers, or coatings.

German OS Nos. 1,597,877 and 1,797,342 disclose extending the spectral sensitivity of selenium layers of electrophotographic recording material in the red spectral range by means of a double layer arrangement which comprises, for example, phthalocyanine dispersion layers. Disadvantages of this system are the considerable technical complications involved in the vapor-phase deposition of the selenium in a vacuum, the brittleness of thicker selenium layers, the poor adhesion between adjacent heterogeneous constituents in these layers, and the difficulty in obtaining dispersions that have uniform wetting capacity to form the layers. Furthermore, because of the absorption behavior and the differing charge-conducting mechanism of selenium and phthalocyanine in the double layer arrangement, optimum photosensitivities cannot be achieved.

U.S. Pat. No. 3,573,906 discloses photoconductive double layers which have an organic and optionally photoconductive insulating coating between the carrier material and the vapor-phase deposited selenium coating for the purpose of achieving adhesion. However, a coating made up in this way inhibits the necessary charge-transfer to a greater extent so that, here also, higher photosensitivities cannot be obtained.

Furthermore, German Auslegeschrift No. 1,964,817 discloses providing selenium coatings, deposited from the vapor phase, with a coating of an organic, photoconductive, insulating material which is not essentially photosensitive in the visible range of the spectrum. In German Patent Specification OS No. 2,120,912, it has been proposed to use, in electrophotographic recording materials, photosensitive coating arrangements which comprise an inorganic material such as cadmium or zinc sulfides, selenides, sulfoselenides or tellurides as the layer producing the charge-carrier, and an organic material having at least 20% of 2,4,7-trinitro-9-fluorenone as the charge-transfer layer. A disadvantage arising in the production of these layers with inorganic photoconductors is that of precisely maintaining the conditions in the vapor phase deposition of selenium, i.e. the precise adjustment of the mixed phases, so that modification of the inorganic materials that leads to good photoconductive properties is achieved. Furthermore, the adherence of selenium to conductive carrier materials such as aluminum, for example, is poor. In addition, the fatigue which occurs during repeated charging and exposure cycles does not permit the use of these layers in electrophotographic copying machines.

Also, Japanese Patent Application No. 43-26710 discloses photoconductive double layers of organic materials on a conductive carrier. In this arrangement, a lower relatively thick layer of a greatly diluted homogeneous solution of a sensitizer in a binder is provided with an upper transparent photosensitive layer. However, a coating made up in this way provides only a relatively small increase in sensitivity which meets the technical requirements only to a limited extent. In another known proposal, disclosed in German Patent Specification OS No. 1,909,742, a particular photoconductive coating is covered several times by pouring a sensitizer solution over it, and the solvent is evaporated. A disadvantage here is that the mechanical stability of the applied coating is low on account of the unsatisfactory cohesion and adhesion of the applied sensitizer. Furthermore, the multiple coating operation is troublesome.

The formation of photoconducting double layers containing a pigment coating has been disclosed in Belgian Pat. Nos. 763,389 andl 763,541, but in this structure use has been made of top layers which do not satisfy the most stringent requirements as regards sensitivity and which do not result in good adhesion between the pigment coating and the top coating; further, the material does not offer sufficient resistance to mechanical damage such as occurs for example in electrophotographic copying machines particularly as a result of the cleaning of the photoconductive coating.

In German Patent Application No. P 2,246,255.1, there is proposed an electrophotographic recording material which contains a photoconductive double layer comprising an organic pigment layer of benzoxanthene-3,4-dicarboxylic acid anhydrides or imides. It has been found, however, that while these photoconductive coatings have improved sensitivity mainly in the visible spectrum range up to 550 nm, the increase in sensitivity over a wider range of the visible spectrum is not satisfactory.

The object of the present invention is to provide an organic photoconductor coating which is photosensitive in the xerographic copying process and which has a wider photosensitivity range of approximately 400–600 nm.

The present invention provides compounds, e.g. condensation products of o-phenylenediamine or 1,8-diaminonaphthalene and 4,10-benzothioxanthene-3,1'-dicarboxylic acid anhydride, having the general formula

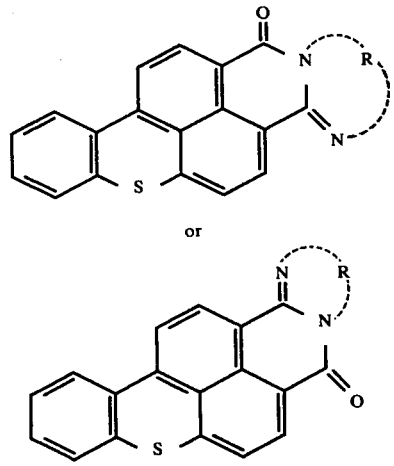

in which R is a substituted or unsubstituted phenyl or naphthyl group. Particularly suitable are compounds wherein R is a phenyl or naphthyl radical.

The compounds possess the required properties and are therefore particularly suitable for use in photoconductive double layers of electrophotographic recording materials. Photoconductive double layers having good photosensitivity are obtained with the electrophotographic recording material of the invention, which coatings possess good mechanical stability and, for example, can be disposed on a cylindrical drum or may be caused to circulate as an endless belt without undergoing any particularly great degree of wear, so that they are suitable for use in electrophotographic copying machines. The unexpectedly great photosensitivity over a wide range of spectrum is believed to result from the fact that the charge-transfer compound present in the transparent top coating is sensitized by the pigment coating, which produces the charge carrier, on account of the charge carriers being absorbed, similarly to electrons or defect electrons, by the top coating, and from the fact that the constitution of the pigments of the invention is particularly adapted to promote this process. The invention accordingly comprises an electrophotographic double layer, one layer of which comprises a compound of the invention.

In a preferred embodiment, the organic pigment layer has a thickness in the range of approximately 0.005 to approximately 2 $\mu$. In this way a high concentration of energized pigment molecules is obtained in the pigment layer and at the boundary surface between the pigment layer and the top layer. Furthermore, the adhesion between the electrically conductive carrier material and the top layer is not adversely affected.

In a preferred embodiment, the transparent top coating has a thickness between approximately 5 and approximately 20 $\mu$. This ensures a sufficiently high charge level.

Any suitable electrically conductive carrier material may be used: such materials includes, for example, aluminum foils or plastic substrates which may be transparent and are vapor-phase coated or faced with aluminum, antimony, bismuth, tin or lead. The choice of metal will be determined by the sensitivities, charging levels, and their constancy during a large number of copying cycles. The type of carrier material also will be determined by the way in which it is used, i.e. whether for example the substrate is to be used in the rigid, self-supporting, or flexible condition.

Layers of pigments of the stated kind are used as homogeneous organic coatings which have a high covering capacity and produce the charge carriers.

The accompanying formula drawings 1 to 5 illustrate preferred compounds, which are condensation products of o-phenylenediamines or 1,8-diaminonaphthalenes which may be substituted or unsubstituted and benzothioxanthene-3,4-dicarboxylic acid anhydrides. Appropriate diamine substituents are, for example, nitro, halo or carboxyalkyl groups. The accompanying formulae 1 to 5 illustrate:

1. 4,10-benzothioxanthene-3,1'-dicarboxylic acid imide-(N,N'-mononitro-phenylene-1,2)-imidine-(3),
2. 4,10-benzothioxanthene-3,1'-dicarboxylic acid imide-(N,N'-monochlorphenylene-1,2)-imidine-(3),
3. 4,10-benzothioxanthene-3,1'-dicarboxylic acid imide-(N,N'-4-methylcarboxyphenylene-1,2)-imidine-(3),
4. 4,10-benzothioxanthene-3,1'-dicarboxylic acid imide-(N,N'-naphthylene-1,8)-imidine-(3),
5. 4,10-benzothioxanthene-3,1'-dicarboxylic acid imide-(N,N'-dinitronaphthylene-1,8)-imidine-(3).

The organic pigment coating is an important part of the recording material in accordance with the invention. It is mainly responsible for determining the spectral photosensitivity of the photoconductive double coating of the invention. The organic pigment coating must be extremely uniform since the uniformity thereof is the only factor that guarantees uniform injection of charge carriers into the top coating.

The pigment coatings are preferably obtained by vapor-phase deposition of the pigment in a vacuum; in this way the coating can be applied in a very densely packed and homogeneous manner.

Such application renders it unnecessary to produce thick pigment coatings for the purpose of achieving high covering capacity. The close arrangement of the molecules of the pigment and the extremely small thickness of the coating permit the charge carriers to be transferred in a particularly advantageous manner. The high extinction of the pigment enables a high concentration of energized pigment molecules to be achieved. Excitation (1) and charge separation (2) occur in the pigment coating in accordance with the following reaction equations:

$$S + h\nu \rightarrow S^x \qquad (1)$$
$$S^x + S \rightarrow \cdot S^{\oplus} + \cdot S^{\ominus} \qquad (2)$$

in which $S$ designates pigment molecules $S^x$ designates energized pigment molecules, and $\cdot S^+$ and $\cdot S^-$ designate pigment radicals.

At the boundary face between the organic pigment layer and the transparent top layer, reaction of energized pigment molecules or pigment radicals with the molecules of the charge transfer compound in the top layer are possible in accordance with the following equations:

$$S^x + F_1 \rightarrow \cdot S^{\ominus} + \cdot F_1^{\oplus} \qquad (3)$$
$$S^x + F_2 \rightarrow \cdot S^{\oplus} + \cdot F_2^{\ominus} \qquad (4)$$
$$\cdot S^+ + F_1 \rightarrow S + \cdot F_1^{\oplus} \qquad (5)$$
$$\cdot S^- + F_2 \rightarrow S + \cdot F_2^{\ominus} \qquad (6)$$

in which $F_1$ designates donor molecules $F_2$ designates acceptor molecules, and $\cdot F_1^+$ and $\cdot F_2^-$ designate donor and acceptor radicals, respectively.

Reactions 3 and 5 occur preferentially when the selected $\pi$-electron system in the top layer is a compound which, being a donor compound, readily can give off electrons. This is the case for example with 2,5-bis-(p-di-ethylaminophenyl)-1,3,4-oxdiazole or polyvinylcarbazole. When the top coating contains a substance which, being an electron acceptor, readily absorbs electrons, such as for example 2,4,7-trinitrofluorenone or 3,6-dinitro-N-t-butyl-naphthalimide, reactions 4 and 6 preferentially occur.

With the present invention, it may suffice, for rendering the pigment effective, if, in addition to its intensive absorption, the compound of the top layer simply has either electron-attracting substituents, such as for example $>C=O$, $>C=N$, $-NO_2$, or $-CF_3$, or electron-repelling substituents, such as for example $-NH_2$, $-N$-alkyl$_2$ or $-O$-alkyl, depending upon whether the pigment is preferentially suitable for reactions 3 and 5 or 4 and 6, since the invention, while using particularly low energy, permits the most favorable continued transfer of the charge carriers within the compact pigment coating, in accordance with the following reactions:

$$\cdot S^{\oplus} + S \rightarrow S + \cdot S^{\oplus} \qquad (7)$$

and $$S + \cdot S^{\ominus} \rightarrow \cdot S^{\ominus} + S, \qquad (8)$$

respectively.

In all previous sensitizing processes on the other hand, transfer through the pigment particles, present in a low concentration, is rendered difficult because of the large gaps between the molecules.

Charge transfer in the covering layer proceeds in a similar manner in accordance with the formulae:

$$\cdot F_1^{\oplus} + F_1 \rightarrow F_1 + \cdot F_1^{\oplus} \text{ (p-conductive)} \qquad (9)$$
$$\cdot F_2^{\ominus} + F_2 \rightarrow F_2 + \cdot F_2^{\ominus} \text{ (n-conductive)} \qquad (10)$$

It follows as a practical consequence of reactions 1–10, that when electron donors are used in the top coating, the double coating arrangement is negatively charged, so that reactions 3, 5, 8 and 9 can take place. Conversely, coatings with electron acceptors in the top layer are positively charged, so that reactions 4, 6, 7 and 10 can take place.

The transparent top layer of organic insulating materials having at least one charge transfer compound will now be described.

The transparent top layer has a high electrical resistance and in the dark prevents loss of electrostatic charge. Upon exposure it transfers the charges produced in the organic pigment layer.

The transparent top layer preferably is composed of a mixture of an electron-donor compound and a bonding agent if a negative charge is to be established, and a mixture of an electron-acceptor compound and a bonding agent if the electrophotographic recording material of the invention is to be used for positive charging.

Accordingly, any electron-donor compounds or electron-acceptor compounds may be used in the transparent top layer. They are used in conjunction with bonding agents or adhesion-promoting agents which are suited to the charge-transfer compound as regards their ability to transfer the charge, and as regards the properties of the film, adhesion, and surface conditions. Furthermore, they may contain known sensitizers or substances that form charge-transfer complexes. These substances may however be used only if they do not adversely affect the necessary transparency of the top coating. Finally, the usual further additives such as flow-inducing agents, softening agents and adhesion-promoting agents may be present.

Organic compounds that have an extended $\pi$-electron system are particularly suitable as the change-transfer compounds. Such organic compounds include both monomeric and polymeric aromatic compounds.

Particularly suitable monomers are those electron-donor compounds which have at least one substituted amino group. Particularly good results have been obtained with heterocyclic compounds such as the oxidazole derivatives mentioned in German Patent No. 1,058,836. These include in particular 2,5-bis-(p-diethylaminophenyl)-oxdiazole-1,3,4. Further suitable monomeric electron-donor compounds are for example triphenylamine derivatives, carbocyclene, benzocondensed heterocyclic pyrazolene derivatives or imidazole derivatives; these also include triazole derivatives and oxazole derivatives, as disclosed in German Pat. Nos. 1,060,260, and 1,120,875, respectively.

Examples of suitable polymers are vinyl aromatic polymers such as polyvinylanthracene, polyacenaphthylene, or copolymers comprising the monomers of these substances and styrene, vinyl acetate and vinyl chloride. Particularly good results have been obtained with poly-N-vinylcarbazole or copolymers comprising N-vinylcarbazole with an N-vinylcarbazole content of at least 40% by weight. Also suitable are formaldehyde condensation products with various aromatic substances such as for example condensates of formaldehyde and 3-bromopyrene.

Apart from the above-mentioned compounds which are predominantly of a p-conductive character, n-conductive compounds also may be used. These electron-acceptors, as they are called, are disclosed for example in German Pat. No. 1,127,218, and German Pat. OS No. 2,059,540. Compounds such as 2,4,7-trinitrofluorenone or 3,6-dinitro-N-t-butyl-naphthalimide have proved particularly successful.

Natural or synthetic resins are suitable as bonding agents from the point of view of flexibility, properties of the film and adhesion. Such materials include in particular polyester resins such as those marketed under the names Dynapol (Trademark—Dynamit Nobel) and Vital (Trademark—PE 200—Goodyear) and consisting of mixed polyesters of iso- and terephthalic acid and glycol. Also, silicon resins which are sold under the name Silicone Resin SR by General Electric and consist of 3-dimensionally cross-linked phenyl-methylsiloxanes have proved suitable. Furthermore, mixed polymers of styrene and maleic acid anhydride, as sold for example under the Registered Trademark Lytron by Monsanto can be employed.

The ratio of charge-transfer compound to bonding agent can be varied. However, because of the need for maximum photosensitivity, i.e. the greatest possible proportion of charge-transfer compound, and on account of the need to prevent the material from crystallizing out, i.e. the need for the greatest possible proportion of bonding agent, relatively strict limits are set. It has been found preferable to use a ratio of approximately 1:1 part by weight, but ratios of between approximately 3:1 and 1:4 or greater are suitable in some cases.

The known sensitizers that additionally may be used may promote charge-transfer in an advantageous manner. Moreover, they may form charge carriers in the transparent top coating. Examples of sensitizers that may be used are Rhodamine B extra, Schultz, Farbstofftabellen, Volume I, seventh Edition, 1931, No. 864, page 365, Brilliant Green, No. 760, page 314, Crystal Violet, No. 785, page 329 and Cryptocyanine, No. 927, page 397. Added compounds which form charge-transfer complexes with the charge-transfer compound also may act in the same way as the sensitizers. In this way a further increase in the photosensitivity of the double layers described can be achieved in certain circumstances. The quanity of added sensitizer or of the compound forming the charge-transfer complex is so selected that the resultant donor-acceptor complex with its charge-transfer bands is still sufficiently transparent for the subjacent organic pigment layer. The optimum concentration range lies within a molar donor/acceptor ratio of approximately 10:1 to approximately 100-1 and vice versa.

Apart from the transparency of the top layer, the thickness thereof is also an important factor as regards the optimum photosensitivity; as previously mentioned, thickness of coating of between approximately 5 and approximately 20 82 are preferred. It has been found, however, that the thickness ranges vary when use is made of monomeric or polymeric charge-transfer compounds in boding agents. Thus, the ranges for monomeric compounds lie more towards greater thicknesses, whereas when polymeric charge-transfer compounds are used, thicknesses in the range of approximately 5 to 10 $\mu$ are sufficient. Very generally, lower maximum charge levels must be expected in the case of thicknesses of coatings of less than approximately 5 $\mu$.

The addition of adhesion-promoting agents alone, as bonding agents, particularly to polymer charge-transfer compounds results in good photosensitivity. In this connection, particularly good results have been obtained with, for example, polyester resins of low molecular weight, such as for example Adhesive 49,000 sold by DuPont.

In the manner described, the top coatings possess the property of enabling a high charge level accompanied by small discharge in the dark to be obtained. Whereas in the case of all existing sensitizing agents, a rise in photosensitivity is associated with an increase in loss of charge in the dark, the system in accordance with the invention at least partly avoids these parallel phenomena. Thus, these coatings can be usefully employed both in electrophotographic copying machines having a low copying speed and a very small lamp power and in machines having high copying rates and correspondingly higher lamp powers.

The accompanying drawings diagrammatically illustrate electrophotographic recording material in which pigment in accordance with the invention is used.

Figure 2:
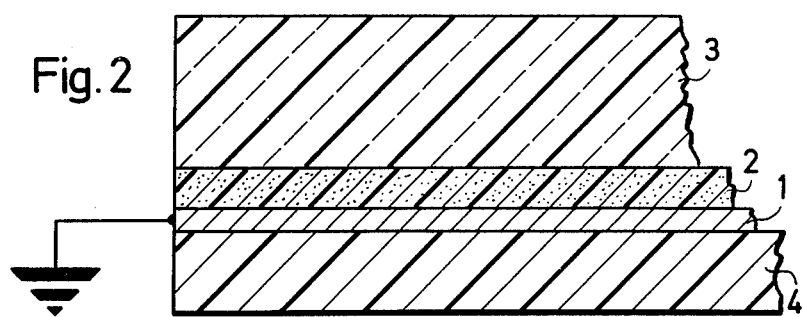

FIG. 1 shows the photoconductive double layer composed of an organic pigment coating 2 forming charge carriers, and of a transparent top coating 3 of insulating organic materials and at least one charge transfer compound on a metallic substrate 1, and FIG. 2 shows the compound on a metallized plastic film 1, 4.

Figure 3:
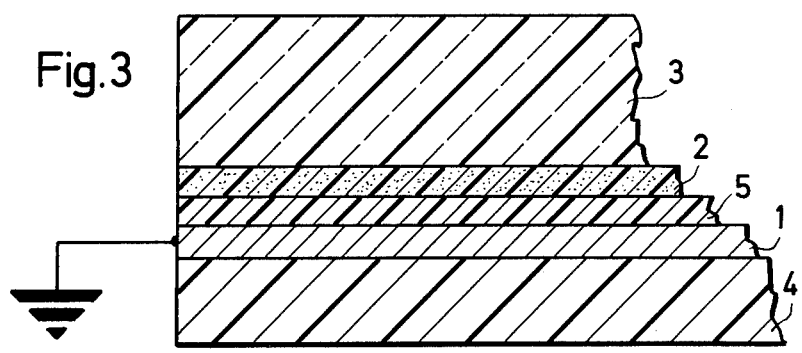

The recording material shown in FIG. 3 is additionally provided with a barrier coating 5 which inhibits charge-carrier leakage in the dark.

Formulae to 1 to 6 show various dyestuffs having utility in the present invention.

It has been found that the use of the pigments of the invention in the pigment coating 2 with the charge-transfer compound contained in the transparent top coating 3 and having an extended $\pi$-electron system, such as for example 2,5-bis-(4'-diethylamino-lphenyl)oxdiazole-1,3,4, and the electrically conductive substrate 1 also enables considerable increases in sensitivity to be obtained as compared with that achieved with a single coating comprising the compound contained in the top coating 3.

The electrophotographic recording material in accordance with the invention is produced by applying a lower pigment coating to the electrically conductive substrate material and by superposing thereon a transparent top coating or organic insulating materials having at least one charge-transfer compound. As already stated, the pigment coating can be applied by the use of special coating methods e.g. by mechanically rubbing the very finely powdered pigment into the electrically conductive substrate material or by depositing an oxidizable leuco base by an electrolytic or electrochemical process or by a spray-gun technique. It has been found however that vapor phase deposition of the pigment in a vacuum is particularly suitable.

In a preferred system, the organic pigment is deposited from the vapor phase at a temperature between 150° to 350° C under a vacuum of approximately $10^{-3}$ to approximately $10^{-6}$ torr, and preferably $10^{-3}$ to $10^{-4}$ torr, on the electrically conductive substrate material. Vapor phase deposition must be carried out in a uniform manner and in as short a time as possible so that the pigment is not damaged by being handled even at higher temperatures.

The duration of the vapor phase deposition operation depends upon various factors such as the temperature that obtains, the pressure used, and the vapor pressure of the pigment. A period of approximately 10 minutes is possible, but it has been found advantageous to use the shortest possible duration of the vapor phase deposition operation, i.e. within a range of approximately 2 to 4 minutes.

When selecting the pigment to be deposited in the vapor phase, it is important that it should be capable of being sublimed or vaporized without decomposing. The pigment can be vaporized by directly heating, but preferably by indirectly heating the surface thereof of a fused mass of the pigment. The distance between the vaporization source and the electrically conductive substrate material is so selected that the temperature of the substrate material is as low as possible and preferably between a room temperature of 20° and 100° C. It is advantageous to cool the substrate material.

The top coating may be applied to the pigment coating by any method, many being known, e.g, by pouring or wiping on the solutions, use being made of solvents which evaporate rapidly, or the method selected being such that rapid evaporation is ensured. The top coating also may be performed in accordance with some other known method, e.g. by lamination coating.

Coating by means of a wide slot nozzle has proved very advantageous. In this way the time during which the solution and the pigment coating are in contact can be considerably limited if for example the substrate to be coated, e.g, in web form, is passed, shortly after application of the solution, into a drying duct, the temperature of which is between 60° and approximately 140° C, depending upon the length thereof and the boiling temperature of the solvent.

Solvents for the above-described top coating materials that have provided particularly good results are tetrahydrofuran, dioxane, and glycol monomethylether (methyl glycol). However, use may be made of other known solvents which easily and rapidly dissolve the top coating materials found to be usable.

The invention will now be described in greater detail by way of example only with reference to the following Examples:

A. PRODUCTION OF PIGMENTS

To produce pigments 1 to 4, the procedure is as follows:

To a suspension of
30.4 g — 4,10-benzothioxanthene-3,1'-dicarboxylic acid anhydride in
400 ml — N-methylpyrrolidone, heated to 100° C, there is dropwise added a solution of
17.41 g — 1,8-naphthylenediamine in
100 ml — N-methylpyrrolidone and 20 ml — glacial acetic acid, ever a period of 15 minutes and while stirring the mixture. After the addition has been completed, the temperature is raised to 150° C and the mixture is heated for a further 5 hours while continuing the stirring. After the mixture of the isomeric pigment (represented by formulae 6a and b) has cooled to room temperature, it is drawn off, washed with methanol, and dried at 60° C in a vacuum drying cabinet. It is obtained in an excellent yield.

Analysis: $C_{28}H_{14}N_2OS$ N(calculated)=6.55 N(determined)=6.5; 6.7.

This produces pigment No. 4; if instead of 1,8-naphthylenediamine, the compounds 4-nitro-1,2-diaminobenzene, 4-chlor-1,2-diaminobenzene or 4-carbomethoxy-1,2-diaminobenzene are used, a comparable yield of the pigments in accordance with the formulae No. 1, 2 or 3 is obtained and their isomers comparable to FIGS. 6a and 6b.

Pigment No. 5 can be obtained from pigment No. 4 in the following way:

42.6 g — of pigment 4 are suspended in
500 ml — 1,2-dichlorethane and
9 ml — nitric acid (e.g. 1.5) are added thereto in drops at room temperature while the mixture is being stirred. After the addition of the nitric acid, stirring is continued for 2 hours at room temperature and then for 5 hours at 50° C. After the pigment suspension has cooled, the isomeric mixture of the nitrated product is drawn off, washed with methanol, and dried at 60° C in a vacuum drying cabinet. It is obtained in an excellent yield .

Analysis: $C_{28}H_{12}H_4O_5S$ N(calculated)=10.8 N(determined)=10.8; 11.0.

B. PRODUCTION OF THE PHOTOCONDUCTIVE COATINGS

The pigments shown in the formula table below were deposited from the vapor phase in a vacuum pump stand (type Al—Messrs. Pfeiffer, Wetzlar) at $10^{-3}$–$10^{-4}$ torr, on a 100$\mu$-thick aluminum foil fitted at a distance of approximately 15 cm. The vaporization temperatures and times are shown, together with the results, in the table below.

For the purpose of testing the electrophotographic properties, a top coating approximately 5 $\mu$ thick was applied to the pigment coating. For this purpose one part by weight of 2,5-bis-(p-diethylaminophenyl)-oxdiazol-1,3,4 and one part by weight of polystyrene resin, e.g. Lytron 820 marketed by Monsanto, were also centrifuged as a 20% by weight solution and then dried for 2 minutes at 120° C.

For measuring the photosensitivity, the double-layer photoconductive coating was charged with a negative voltage and the coating was then illuminated with an XBO 150 xenon lamp marketed by Messrs. Osram; the beamed energy was approximately 300$\mu$W cm$^{-2}$; the charging level and the photo-induced brilliancy-decline curve of the photoconductive coating were measured with a 610 B electrometer made by Messrs. Keithley Instruments, USA, and by a probe in accordance with the method described by Arneth and Lorenz in Reprographie 3, 199 (1963). The charge level ($U_0$) and that time ($T\frac{1}{2}$) after which the half-charge $U_0/2$ is reached were taken as factors characterizing the photoconductive coating.

For comparison purposes the values are given for a reference coating constituted by a photoconductive coating without the pigment coating otherwise used.

The values recorded are shown in the table below.

To provide a further comparison with the pigments claimed in German Patent Application P 22 46 255.1, there are given the following energies that are necessary for reducing an initial charge of 600–800 V of the described coatings to one-half of this charge. The values given are in units of $10^{-6}$ WS cm$^{-2}$ for the longer two wavelengths in the longer region.

| Pigment | Vapor phase deposition time, (minutes) | 606 nm | 552 nm |
|---|---|---|---|
| 1 | 4 | 5.9 | 6.0 |
| Benzothioxanthene-3,4-dicarboxylic acid-N-(3-nitrophenyl)-imide, in accordance with German Patent Application P 22 46 255.1 | 4 | >15 | 10.5 |

The greater these energies, the lower is the sensitivity in the spectrum range in question; the considerable advantage of the compounds claimed will be seen herefrom.

TABLE

Electrophotographic properties of double pigment coatings

| Pigment | Vapor-phase deposition temperatures and times | | $U_o$ | $T\frac{1}{2}$ |
|---|---|---|---|---|
|  | °C | min. | V | m sec. |
| 1 | 250 | 2 | 880 | 60 |
| 1 | 250 | 4 | 920 | 32 |
| 2 | 230 | 2 | 800 | 115 |
| 2 | 230 | 4 | 860 | 95 |
| 3 | 260 | 2 | 880 | 105 |
| 3 | 260 | 4 | 870 | 85 |
| 5 | 300 | 2 | 810 | 240 |
| 5 | 300 | 4 | 780 | 120 |
| — | — | — | 420 | >1000 |

It will be obvious to those skilled in the art that many modifications may be made within the scope of the present invention without departing from the spirit thereof, and the invention includes all such modifications.

What is claimed is:

1. An electrophotographic recording material comprising an electrically conductive carrier material having a photoconductive double layer thereon composed of an organic pigment layer of a thickness in the range of about 0.005 to about 2$\mu$m and a transparent top layer of organic insulating materials having at least one charge transfer compound in which the organic pigment layer is composed of a compound of at least one of the formulae

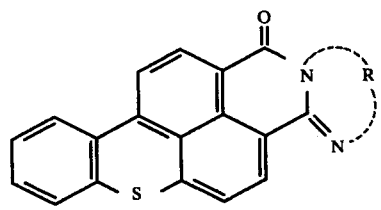

I

-continued

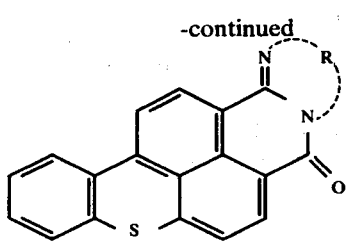

II wherein R is one of the groups

 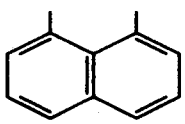

which may be substituted.

2. A recording material according to claim 1 wherein the groups

 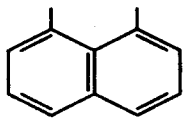

are substituted by one or more nitro, halogen or alkoxycarbonyl groups.

3. A recording material according to claim 1 in which the organic pigment layer is composed of a condensation product of 4,10-benzothioxanthene-3,1'-dicarboxylic anhydride and an o-phenylene-diamine or a 1,8-diaminonaphthalene.

4. A recording material according to claim 1 in which the organic pigment layer is composed of a condensation product of 4,10-benzothioxanthene-3,1'-dicarboxylic acid anhydride and mononitrophenylenediamine-(1,2).

5. A recording material according to claim 1 in which the organic pigment layer is composed of a condensation product of 4,10-benzothioxanthene-3,1'-dicarboxylic acid anhydride and monochlorphenylenediamine-(1,2).

6. A recording material according to claim 1 in which the organic pigment layer is composed of a condensation product of 4,10-benzothioxanthene-3,1'-dicarboxylic acid anhydride and 4-methyloxycarbonyl-phenylenediamine-(1,2).

7. A recording material according to claim 1 in which the organic pigment layer is composed of a condensation product of 4,10-benzothioxanthene-3,1'-dicarboxylic acid anhydride and dinitronaphthylenediamine-(1,8).

8. A recording material according to claim 1 wherein the organic pigment layer is applied by vacuum deposition.

9. A recording material as claimed in claim 1 having a transparent layer from 5 to 20 μm thick.

* * * * *